(12) United States Patent
Hammerschmidt et al.

(10) Patent No.: US 8,384,399 B2
(45) Date of Patent: Feb. 26, 2013

(54) SYSTEM INCLUDING CAPACITIVELY COUPLED ELECTRODES AND CIRCUITS IN A NETWORK

(75) Inventors: Dirk Hammerschmidt, Villach (AT); Thomas Klug, Augsburg (DE)

(73) Assignee: Infineon Technologies AG, Neubiberg (DE)

( * ) Notice: Subject to any disclaimer, the term of this patent is extended or adjusted under 35 U.S.C. 154(b) by 194 days.

(21) Appl. No.: 12/200,234

(22) Filed: Aug. 28, 2008

(65) Prior Publication Data

US 2010/0054305 A1 Mar. 4, 2010

(51) Int. Cl.
*G01R 27/26* (2006.01)
(52) U.S. Cl. ............ 324/667; 340/545.2; 340/667; 280/735; 257/712; 455/117; 455/41.1
(58) Field of Classification Search .................. 324/667
See application file for complete search history.

(56) References Cited

U.S. PATENT DOCUMENTS

| | | | |
|---|---|---|---|
| 6,051,981 A * | 4/2000 | Gershenfeld et al. | 324/663 |
| 6,282,407 B1 * | 8/2001 | Vega et al. | 455/41.1 |
| 6,397,136 B1 | 5/2002 | Breed et al. | |
| 6,529,809 B1 | 3/2003 | Breed et al. | |
| 6,960,919 B2 * | 11/2005 | Barmettler | 324/539 |
| 6,995,670 B2 | 2/2006 | Wadlow et al. | |
| 7,205,780 B2 * | 4/2007 | Pasero et al. | 324/667 |
| 2002/0129633 A1 * | 9/2002 | Joki et al. | 72/13.4 |
| 2003/0036835 A1 * | 2/2003 | Breed et al. | 701/45 |
| 2004/0222803 A1 * | 11/2004 | Tartagni | 324/662 |
| 2005/0043876 A1 * | 2/2005 | Fultz et al. | 701/45 |
| 2006/0065973 A1 * | 3/2006 | Dallenbach et al. | 257/712 |
| 2006/0066319 A1 * | 3/2006 | Dallenbach et al. | 324/662 |
| 2006/0097733 A1 * | 5/2006 | Roziere | 324/662 |
| 2006/0205106 A1 * | 9/2006 | Fukuda et al. | 438/52 |
| 2006/0262101 A1 * | 11/2006 | Layton et al. | 345/173 |
| 2006/0267321 A1 * | 11/2006 | Harish et al. | 280/735 |
| 2006/0267598 A1 * | 11/2006 | Morimoto | 324/661 |
| 2007/0026804 A1 * | 2/2007 | Ishibashi et al. | 455/63.1 |

(Continued)

FOREIGN PATENT DOCUMENTS

| | | |
|---|---|---|
| CN | 1889138 | 1/2007 |
| DE | 10117142 | 10/2002 |
| EP | 0872713 | 10/1998 |
| FR | 2817352 | 5/2002 |
| SU | 0905881 | 2/1982 |
| WO | WO2004047630 A1 | 6/2004 |

OTHER PUBLICATIONS

"Seat Occupancy Detection Using Capacitive Sensing Technology", Hubert Zangl, et al., Society of Automotive Engineers, Inc., 2007 (7 pgs.).

*Primary Examiner* — Melissa Koval
*Assistant Examiner* — Benjamin M Baldridge
(74) *Attorney, Agent, or Firm* — Dicke, Billig & Czaja, PLLC

(57) ABSTRACT

A system including a first electrode, a second electrode, a first circuit and a second circuit. The second electrode is capacitively coupled to the first electrode. The first circuit is configured to receive data via a network and transmit a signal via the first electrode based on the data. The second circuit is configured to receive data via the network and receive a current that corresponds to the signal via the second electrode based on the data.

14 Claims, 3 Drawing Sheets

U.S. PATENT DOCUMENTS

| | | | |
|---|---|---|---|
| 2007/0171055 A1* | 7/2007 | Laakso et al. | 340/545.2 |
| 2007/0184788 A1* | 8/2007 | Minotani et al. | 455/117 |
| 2008/0109956 A1* | 5/2008 | Bayley et al. | 4/623 |
| 2008/0186192 A1* | 8/2008 | Yamanaka et al. | 340/667 |
| 2008/0202251 A1* | 8/2008 | Serban et al. | 73/780 |
| 2009/0033078 A1* | 2/2009 | Hawes et al. | 280/735 |
| 2009/0194406 A1* | 8/2009 | Scheckenbach | 200/85 A |
| 2010/0004063 A1* | 1/2010 | Rebmann | 463/39 |

* cited by examiner

US 8,384,399 B2

SYSTEM INCLUDING CAPACITIVELY COUPLED ELECTRODES AND CIRCUITS IN A NETWORK

BACKGROUND

Capacitive sensor technology has proven to be a reliable measurement technology that is suitable for demanding environments. Capacitive sensors are used in many applications, such as industrial, automotive, medical and consumer applications.

Sometimes, capacitive sensors are used for distance measurement and position detection. A changing electric field is created between at least two electrodes and the corresponding displacement current or shift current is measured. The capacitance or capacitive coupling network between electrodes is calculated via the relationship between voltage and current. An object brought into the electric field changes the dielectric between the electrodes and the measurement in at least one of three ways. The object may change the permittivity, the electrical conductance and/or surge part of the electric field to ground.

Using multiple electrodes, an electrical tomography of the space between electrodes can be produced. In larger rooms, the distance between electrodes and the length of the wires or connection lines to front-end electronics increases such that the connection lines emit electrical fields and/or act as antennas to pick up electromagnetic interference (EMI). Sometimes, the connection lines are shielded to prevent emitting electrical fields and acting as antennas. However, shielding increases load capacitances to the voltage driver that builds up voltages between electrodes. The increased load capacitance limits transmit frequency and increases the field independent part of the displacement currents, which reduces sensitivity of the measurement system. On the receiver side, the parasitic input capacitance may be much higher than the capacitance to be measured, which leads to a strong attenuation (capacitive divider) and reduces resolution.

For these and other reasons, there is a need for the present invention.

SUMMARY

One embodiment described in the disclosure provides a system including a first electrode, a second electrode, a first circuit and a second circuit. The second electrode is capacitively coupled to the first electrode. The first circuit is configured to receive data via a network and transmit a signal via the first electrode based on the data. The second circuit is configured to receive data via the network and receive a current that corresponds to the signal via the second electrode based on the data.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Figure 1:
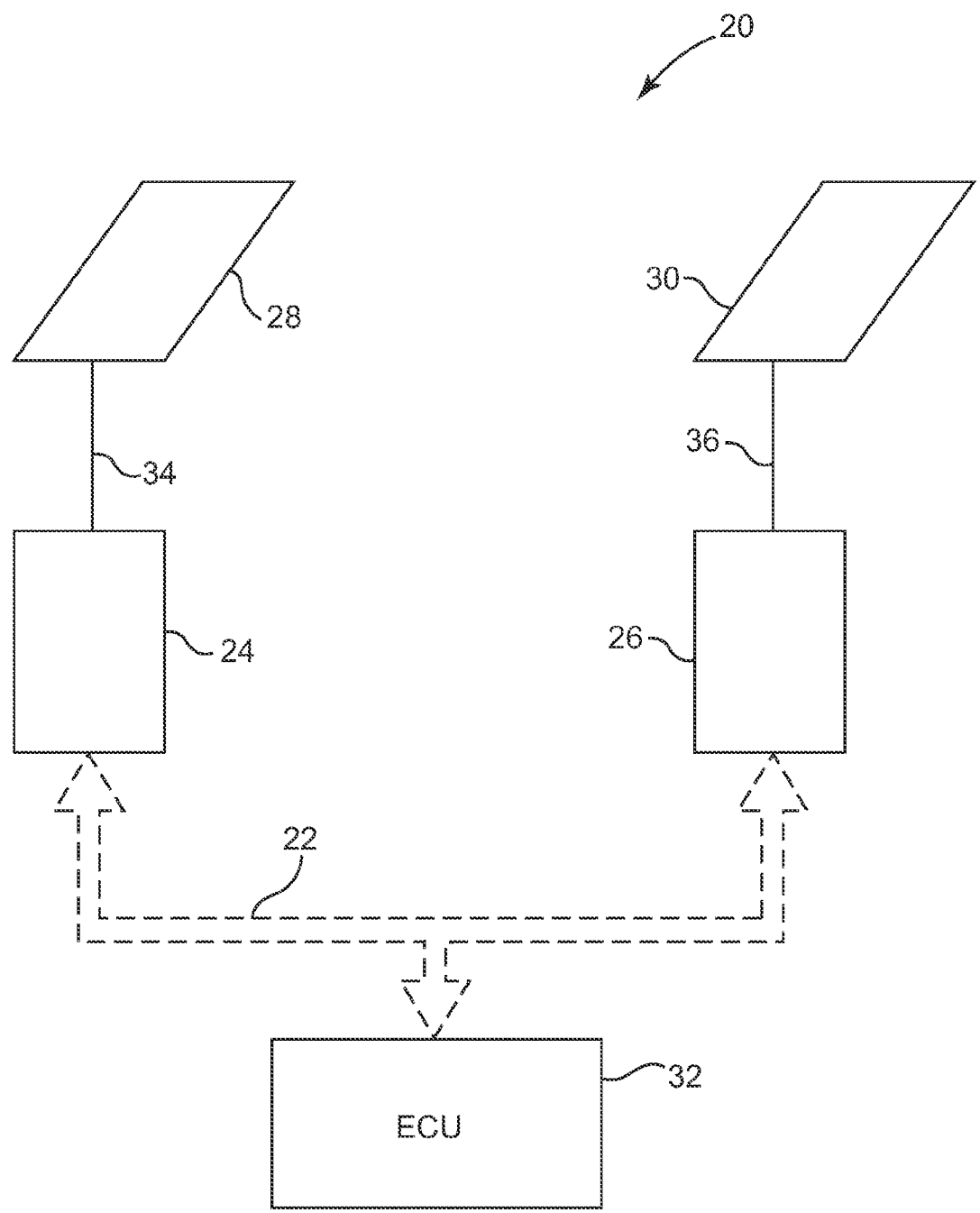
FIG. 1 is a diagram illustrating one embodiment of a capacitive sensor system including a network.

FIG. 1 is a diagram illustrating one embodiment of a capacitive sensor system 20 including a network 22. Capacitive sensor system 20 includes a first circuit 24, a second circuit 26, a first electrode 28, a second electrode 30 and an electronic control unit (ECU) 32. In other embodiments, capacitive sensor system 20 includes any suitable number of circuits, such as first circuit 24 and second circuit 26, and any suitable number of electrodes, such as first electrode 28 and second electrode 30. In one embodiment, capacitive sensor system 20 includes multiple electrodes connected to first circuit 24 and/or multiple electrodes connected to second circuit 26. In one embodiment, capacitive sensor system 20 includes a group of electrodes coupled to first circuit 24 and/or a group of electrodes coupled to second circuit 26.

Capacitive sensor system 20 measures the capacitance between first electrode 28 and second electrode 30, where the measured capacitance is used to determine whether the dielectric and/or the distance changed between first and second electrodes 28 and 30. In one embodiment, capacitive sensor system 20 is used to measure distance. In one embodiment, capacitive sensor system 20 is used to detect the position of an object. In one embodiment, capacitive sensor system 20 is used in a seat occupancy application, such as an automotive airbag system.

Network 22 is used to configure the measurements by selecting one of the first and second circuits 24 and 26 to be a transmitter and the other to be a receiver. Parameters that can be shared during setup include frequency, amplitudes, phase delay, spread spectrum settings, receiver gain, filter bandwidth, integration time and sampling rate. After measurements are taken, network 22 is used to collect the measurement results from the receiver.

First circuit 24 is electrically coupled to first electrode 28 via first connection line 34, and second circuit 26 is electrically coupled to second electrode 30 via second connection line 36. First electrode 28 is capacitively coupled to second electrode 30.

Each of the first and second circuits 24 and 26 are coupled to a power supply (not shown). In one embodiment, first circuit 24 and second circuit 26 are each powered via a separate power supply. In one embodiment, first circuit 24 and second circuit 26 are powered via a shared power supply. In one embodiment, at least one of first circuit 24 and second circuit 26 are powered via inductive coupling.

ECU 32 is communicatively coupled to first circuit 24 and second circuit 26 via network 22. In one embodiment, network 22 includes a bus connected to at least one of first circuit 24 and second circuit 26. In one embodiment, network 22 includes a wireless communications link for communicating to at least one of first circuit 24 and second circuit 26. In one embodiment, network 22 includes inductive coupling for communicating to at least one of first circuit 24 and second circuit 26.

ECU 32 transmits digital data to first circuit 24 and second circuit 26 via network 22. The transmitted data includes information about the electronic signal to be transmitted between electrodes 28 and 30. In one embodiment, ECU 32 transmits data that includes a signal start time. In one embodiment, ECU 32 transmits data that includes a signal frequency. In one embodiment, ECU 32 transmits data that includes a spread spectrum sequence or a spread spectrum set-up for the signal.

First circuit 24 and second circuit 26 each include a driver unit and/or a measurement unit. First circuit 24 receives the data and either transmits a signal via a driver unit or receives displacement current that corresponds to a transmitted signal via a measurement unit. First circuit 24 transmits the signal and receives displacement current via first electrode 28. Second circuit 26 receives the data and either transmits a signal via a driver unit or receives displacement current that corresponds to a transmitted signal via a measurement unit. Second circuit 26 transmits the signal and receives displacement current via second electrode 28. In one embodiment, first circuit 24 is a transmitter that includes a driver unit. In one embodiment, first circuit 24 is a receiver that includes a measurement unit. In one embodiment, first circuit 24 is a transceiver that includes a driver unit and a measurement unit. In one embodiment, second circuit 26 is a transmitter that includes a driver unit. In one embodiment, second circuit 26 is a receiver that includes a measurement unit. In one embodiment, second circuit 26 is a transceiver that includes a driver unit and a measurement unit.

In one embodiment, first circuit 24 is a transceiver electrically coupled to multiple electrodes in a first local group and second circuit 26 is a transceiver electrically coupled to multiple electrodes in a second local group. The electrodes in the first local group are capacitively coupled to the electrodes in the second local group. First circuit 24 selects at least one of the electrodes in the first local group for transmitting and/or receiving signals and second circuit 26 selects at least one of the electrodes in the second local group for transmitting and/or receiving signals. ECU 32 transmits data to first circuit 24 and second circuit 26, which receive the data and transmit signals and receive currents based on the data to measure capacitance between the selected electrodes.

In operation of one embodiment, ECU 32 transmits the data and first circuit 24 receives the data via network 22 and transmits a signal via first electrode 28 based on the data. Second circuit 26 receives the data via network 22 and second circuit 26 receives a displacement current that corresponds to the transmitted signal via second electrode 30 and based on the data. First circuit 24 uses the data to select a signal frequency, switch frequencies via a spread spectrum sequence and to start the signal at a specified time. Second circuit 26 uses the data to configure itself to expect displacement current after the start time of the signal and to demodulate the received displacement current based on the selected frequency and spread spectrum sequence.

Figure 2:
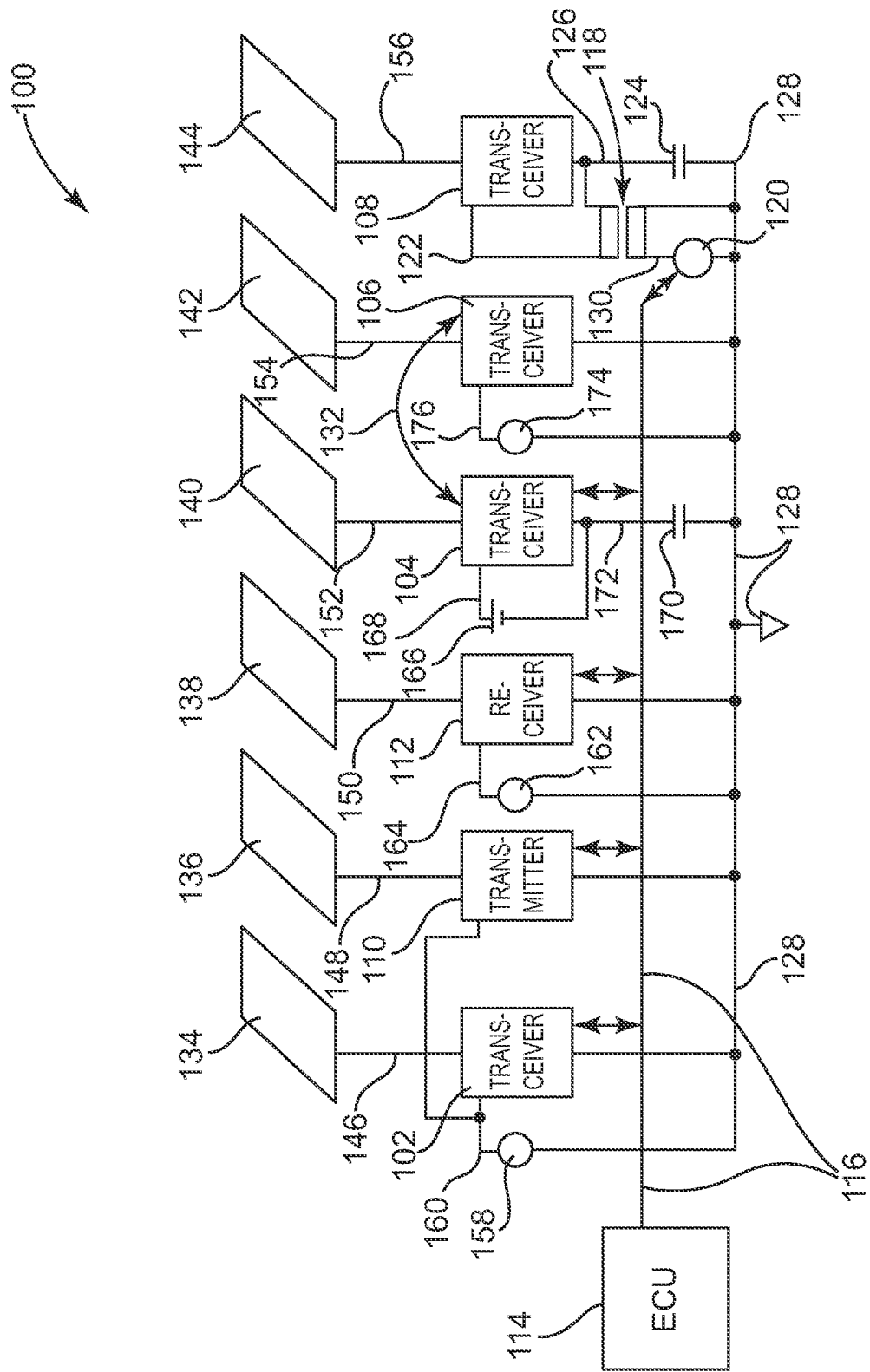
FIG. 2 is a diagram illustrating one embodiment of a capacitive sensor system including multiple transceivers, a transmitter and a receiver.

FIG. 2 is a diagram illustrating one embodiment of a capacitive sensor system 100 including multiple transceivers 102, 104, 106 and 108, a transmitter 110 and a receiver 112. Capacitive sensor system 100 is similar to capacitive sensor system 20 of FIG. 1. In one embodiment, capacitive sensor system 100 is used to measure distance. In one embodiment, capacitive sensor system 100 is used to detect the position of at least one object. In one embodiment, capacitive sensor system 100 is used in a seat occupancy application, such as an automotive airbag system.

Capacitive sensor system 100 includes first transceiver 102, second transceiver 104, transmitter 110, receiver 112 and ECU 114 electrically coupled to bus 116. Also, fourth transceiver 108 is inductively coupled to bus 116 via transformer 118 and transformer interface circuit 120. Fourth transceiver 108 receives data and power from transformer 118. Fourth transceiver 108 is electrically coupled to one side of transformer 118 via coupling line 122. Fourth transceiver 108 and this one side of transformer 118 are electrically coupled to one side of a first capacitor 124 via capacitor connection line 126. The other side of first capacitor 124 is electrically coupled to a reference, such as ground, at 128. Fourth transceiver 108 is electrically coupled to the reference at 128 through first capacitor 124 to reduce impedance to ground for the higher signal frequencies used to measure the capacitance between electrodes. The other side of transformer 118 is electrically coupled to transformer interface circuit 120 via interface line 130, and the transformer interface circuit 120 and this other side of transformer 118 are electrically coupled to the reference at 128. In addition, transformer interface circuit 120 is electrically coupled to bus 116. In one embodiment, bus 116 is a controller-area network (CAN-bus). In one embodiment, bus 116 is a local interconnect network (LIN-bus).

ECU 114 transmits data and communicates with first transceiver 102, second transceiver 104, transmitter 110 and receiver 112 via bus 116. ECU 114 transmits data and communicates with fourth transceiver 108 via transformer interface circuit 120, where transformer interface circuit 120 receives the data and transmits the data to transformer 118, which transfers the data to fourth transceiver 108.

Second transceiver 104 and third transceiver 106 are communicatively coupled via a radio frequency (RF) communications link 132. ECU 114 transmits data to second transceiver 104 via bus 116 and second transceiver 104 relays the data to third transceiver 106 via RF communications link 132. Using a bus and/or an RF communications link, circuits, such as transmitter 110, receiver 112 and transceivers 102, 104, 106 and 108, and their corresponding electrodes can be remotely located without using long driver lines and/or long receiver lines to the electrodes.

The network including bus 116, transformer interface circuit 120 and transformer 118, and RF communications link 132 is used to configure the measurements by selecting one or more of the transceivers 102, 104, 106 and 108 and/or transmitter 110 to transmit signals and one or more of the transceivers 102, 104, 106 and 108 and/or receiver 112 to receive signals. Parameters that can be shared during setup include frequency, amplitudes, phase delay, spread spectrum settings, receiver gain, filter bandwidth, integration time and sampling rate. After measurements are taken, the network is used to collect the measurement results from the selected receiver(s).

Capacitive sensor system 100 includes a first electrode 134, a second electrode 136, a third electrode 138, a fourth electrode 140, a fifth electrode 142 and a sixth electrode 144. First transceiver 102 is electrically coupled to first electrode 134 via first connection line 146. Transmitter 110 is electrically coupled to second electrode 136 via second connection line 148. Receiver 112 is electrically coupled to third electrode 138 via third connection line 150. Second transceiver 104 is electrically coupled to fourth electrode 140 via fourth connection line 152. Third transceiver 106 is electrically coupled to fifth electrode 142 via fifth connection line 154. Fourth transceiver 108 is electrically coupled to sixth electrode 144 via sixth connection line 156. Electrodes 134, 136, 138, 140, 142 and 144 are capacitively coupled to each other and capacitive sensor system 100 measures the capacitance between any two of the electrodes 134, 136, 138, 140, 142 and 144. The measured capacitance can be used to determine whether the dielectric and/or the distance changed between electrodes.

In other embodiments, capacitive sensor system 100 includes any suitable number of transceivers, transmitters and/or receivers and any suitable number of electrodes coupled to each of the transceivers, transmitters and/or receivers. In one embodiment, at least one of the transceivers, transmitters and/or receivers has multiple electrodes coupled to it. In one embodiment, each of the transceivers, transmitters and/or receivers has a different group of one or more electrodes coupled to it. Power can be provided to transceivers 102, 104, 106 and 108, transmitter 110 and receiver 112 in a number of ways. In one embodiment, power is supplied via separate power supplies. In one embodiment, power is supplied via shared power supplies. In one embodiment, power is supplied via power sources, such as batteries, generators, a board net and/or solar cells. In one embodiment, power is supplied via coupling, such as inductive coupling or capacitive coupling.

Also, the reference at 128 can be realized in a number of ways. In one embodiment, the reference at 128 is realized via wires. In one embodiment, the reference at 128 is realized via the chassis of an automobile.

In addition, power supplies can be used for communicating to the connected device(s). In one embodiment, power supply and ground lines are used for communicating via modulating supply current and/or voltage. In one embodiment, power supply and ground lines are used for communicating via multiplexing between supplying power and communication phases.

A first power supply 158 is electrically coupled to first transceiver 102 and transmitter 110 via power supply line 160. First power supply 158 provides power to first transceiver 102 and transmitter 110 via power supply line 160. First power supply 158, first transceiver 102 and transmitter 110 are electrically coupled to the reference at 128.

A second power supply 162 is electrically coupled to receiver 112 via power supply line 164. Second power supply 162 supplies power to receiver 112 via power supply line 164. Second power supply 162 and receiver 112 are electrically coupled to the reference at 128.

A battery 166 is electrically coupled to second transceiver 106 via power supply line 168. Battery 166 provides power to transceiver 106 via power supply line 168. Battery 166 and second transceiver 104 are electrically coupled to one side of a second capacitor 170 via capacitor connection line 172. The other side of second capacitor 170 is electrically coupled to the reference at 128. In other embodiments, battery 166 and second transceiver 104 are electrically coupled directly to the reference at 128.

A third power supply 174 is electrically coupled to third transceiver 106 via power supply line 176. Third power supply 174 provides power to third transceiver 106 via power supply line 176. Third power supply 174 and third transceiver 106 are electrically coupled to the reference at 128.

ECU 114 transmits digital data to first transceiver 102, second transceiver 104, transmitter 110 and receiver 112 via bus 116. ECU 114 transmits data to third transceiver 106 by transmitting the data to second transceiver 104 via bus 116 and second transceiver 104 forwards the data to third transceiver 106 via RF communications link 132. ECU transmits data to fourth transceiver 108 by transmitting the data to transformer interface circuit 120 via bus 116 and transformer interface circuit 120 provides the data to transformer 118, which transfers the data to fourth transceiver 108. The transmitted data includes information about the electronic signal to be transmitted between electrodes 134, 136, 138, 140, 142 and 144. In one embodiment, ECU 114 transmits data that includes a signal start time. In one embodiment, ECU 114 transmits data that includes a signal frequency. In one embodiment, ECU 114 transmits data that includes a spread spectrum sequence or a spread spectrum set-up for the signal. In one embodiment, ECU 114 transmits data that selects at least one of the transceivers 102, 104, 106 and 108 or transmitter 110 for transmitting the electrical signal and at least one of the transceivers 102, 104, 106 and 108 or receiver 112 for receiving the displacement current that corresponds to the transmitted signal.

Each of the transceivers 102, 104, 106 and 108 includes a driver unit and a measurement unit. Transceivers 102, 104, 106 and 108 receive the data and either transmit a signal via a driver unit, receive displacement current that corresponds to a transmitted signal via a measurement unit or remain idle based on the data. Transceivers 102, 104, 106 and 108 transmit signals and receive displacement currents via electrodes 134, 140 142 and 144, respectively.

Transmitter 110 includes a driver unit and receiver 112 includes a measurement unit. Transmitter 110 receives the data and transmits a signal via a driver unit or remains idle based on the data. Receiver 112 receives the data and receives displacement current that corresponds to a transmitted signal via a measurement unit or remains idle based on the data. Transmitter 110 transmits signals via electrode 136 and receiver 112 receives displacement current via electrode 138.

In operation, ECU 114 transmits data via bus 116. ECU 114 selects at least one of the transceivers 102, 104, 106 and 108 or transmitter 110 to transmit electrical signals via the corresponding electrode(s). ECU 114 selects at least one of the transceivers 102, 104, 106 and 108 or receiver 112 to receive displacement current via the corresponding electrode (s). The transceivers 102, 104, 106 and 108, transmitter 110 and receiver 112 receive the data and transmit signals and receive currents based on the data to measure capacitance between the selected electrodes.

The transmitted data includes information about the electronic signal to be transmitted between electrodes 134, 136, 138, 140, 142 and 144. Each transmitting circuit uses the information to transmit an electrical signal and each receiving circuit uses the information to configure itself to receive the displacement current corresponding to the transmitted signal and to demodulate the received displacement current. In one embodiment, ECU 114 transmits data that includes a signal start time. In one embodiment, ECU 114 transmits data that includes a signal frequency. In one embodiment, ECU 114 transmits data that includes a spread spectrum sequence of the signal.

Figure 3:
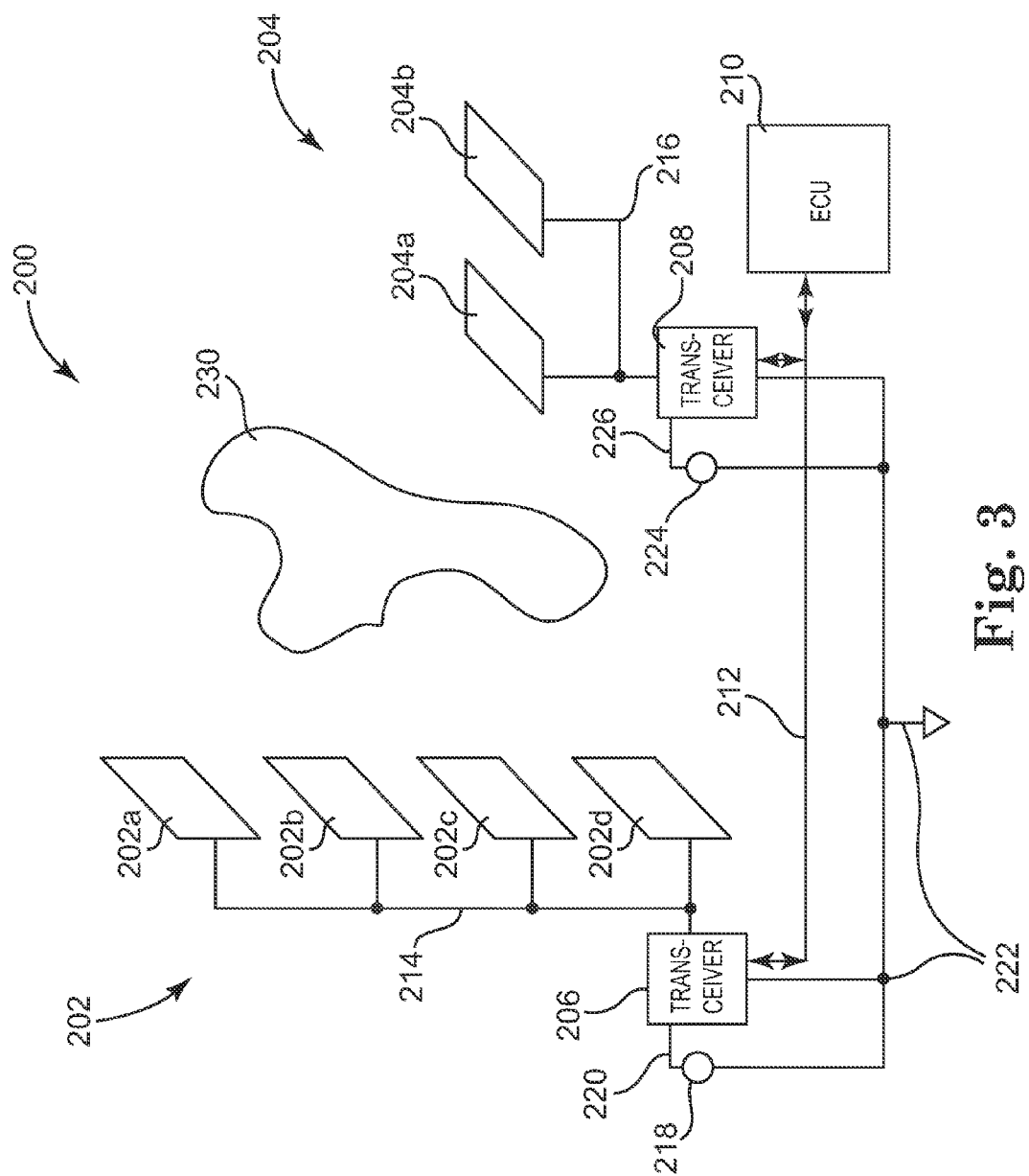
FIG. 3 is a diagram illustrating one embodiment of a capacitive sensor system including two local groups of electrodes.

FIG. 3 is a diagram illustrating one embodiment of a capacitive sensor system 200 including two local groups of electrodes 202 and 204. Capacitive sensor system 200 measures the capacitance between electrodes in the two local groups of electrodes 202 and 204, where the measured capacitance is used to determine whether the dielectric and/or the distance changed between electrodes. Capacitive sensor system 200 is similar to capacitive sensor system 20 of FIG. 1 and capacitive sensor system 100 of FIG. 2. In one embodiment, capacitive sensor system 200 is used to measure distance. In one embodiment, capacitive sensor system 200 is used to detect the position of at least one object. In one embodiment, capacitive sensor system 200 is used in a seat occupancy application, such as an automotive airbag system.

Capacitive sensor system 200 includes a first transceiver 206, a second transceiver 208 and an ECU 210 electrically coupled to a network bus 212. ECU 210 transmits data and communicates with first transceiver 206 and second transceiver 208 via bus 212. First transceiver 206 is electrically coupled to electrodes 202a-202d in the first local group of electrodes 202 via electrode connection lines 214. Second transceiver 208 is electrically coupled to electrodes 204a and 204b in the second local group of electrodes 204 via electrode connection lines 216. Electrodes 202a-202d, 204a and 204b are capacitively coupled to each other. Capacitive sensor system 200 measures the capacitance between any two of the electrodes 202a-202d, 204a and 204b. The measured capacitance can be used to determine whether the dielectric and/or the distance changed between electrodes 202a-202d, 204a and 204b.

A first power supply 218 is electrically coupled to first transceiver 206 via power supply line 220. First power supply 218 provides power to first transceiver 206 via power supply line 220. First power supply 218 and first transceiver 206 are electrically coupled to a reference, such as ground, at 222.

A second power supply 224 is electrically coupled to second transceiver 208 via power supply line 226. Second power supply 224 provides power to second transceiver 208 via power supply line 226. Second power supply 224 and second transceiver 208 are electrically coupled to the reference at 222.

ECU 210 transmits digital data to first transceiver 206 and second transceiver 208 via bus 212. The transmitted data includes information about the electronic signal to be transmitted between electrodes 202a-202d, 204a and 204b. In one embodiment, ECU 210 transmits data that includes a signal start time. In one embodiment, ECU 210 transmits data that includes a signal frequency. In one embodiment, ECU 210 transmits data that includes a spread spectrum sequence or a spread spectrum set-up for the signal. In one embodiment, ECU 210 transmits data that selects one of the transceivers 206 and 208 for transmitting the electrical signal and the other of the transceivers 206 and 208 for receiving the displacement current that corresponds to the transmitted signal. In one embodiment, ECU 210 transmits data that selects at least one of the electrodes 202a-202d coupled to first transceiver 206 and at least one of the electrodes 204a and 204b coupled to second transceiver 208.

Each of the transceivers 206 and 208 includes a driver unit and a measurement unit. Transceivers 206 and 208 receive the data and either transmit a signal via a driver unit, receive displacement current that corresponds to a transmitted signal via a measurement unit or remain idle based on the data. First transceiver 206 transmits signals and receives current via electrodes 202a-202d, and second transceiver 208 transmits signals and receives current via electrodes 204a and 204b.

In operation of one embodiment, ECU 210 transmits data via bus 212. ECU 210 selects one of the transceivers 206 and 208 to transmit electrical signals and the other one of the transceivers 206 and 208 to receive displacement current that corresponds to the transmitted signals. ECU 210 also selects at least one of the electrodes 202a-202d coupled to first transceiver 206 and at least one of the electrodes 204a and 204b coupled to second transceiver 208. Transceivers 206 and 208 receive the data and transmit signals and receive currents based on the data to measure capacitance between the selected electrodes. If an object, such as object 230, moves between the selected electrodes, the dielectric and the capacitance between the selected electrodes changes and the object can be detected and measured.

The data transmitted via ECU 210 includes information to select which of the transceivers 206 and 208 transmits and which of the transceivers 206 and 208 receives. The data transmitted via ECU 210 also includes information to select which electrodes 202a-202d, and 204a and 204b are used to take the capacitance measurement. In addition, the data transmitted via ECU 210 includes information about the electronic signal to be transmitted. The transmitting one of the transceivers 206 and 208 uses the information to transmit an electrical signal and the receiving one of the transceivers 206 and 208 uses the information to configure itself to receive the displacement current corresponding to the transmitted signal and to demodulate the received displacement current. In one embodiment, ECU 210 transmits data that includes a signal start time. In one embodiment, ECU 210 transmits data that includes a signal frequency. In one embodiment, ECU 210 transmits data that includes a spread spectrum sequence of the signal. In other embodiments, the transmitted data does not include information to select which of the transceivers 206 and 208 transmits and which of the transceivers 206 and 208 receives and/or information to select which electrodes are used.

Using bus 212, first transceiver 206 and electrodes 202a-202d and second transceiver 208 and electrodes 204a and 204b can be remotely located without using long driver lines and/or long receiver lines to electrodes 202a-202d, 204a and 204b.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A system comprising:
   a first electrode;
   a second electrode situated a first distance from the first electrode and capacitively coupled to the first electrode;
   a third electrode situated a second distance from the first electrode and capacitively coupled to the first electrode and situated a third distance from the second electrode and capacitively coupled to the second electrode;
   a first circuit configured to receive data via a network and transmit a first signal via the first electrode, wherein the first circuit is configured to transmit based on the data;
   a second circuit configured to receive the data via the network and directly coupled to the second electrode to receive a first current from the second electrode and to transmit a second signal via the second electrode, wherein the first current corresponds to the first signal and the second circuit is configured to receive and transmit based on the data;
   a third circuit configured to receive the data via the network and directly coupled to the third electrode to receive a second current from the third electrode and to receive a third current from the third electrode, wherein the second current corresponds to the first signal and the third current corresponds to the second signal and the third circuit is configured to receive based on the data; and an electronic control unit configured to communicate with the first circuit and the second circuit and the third circuit via the network and detect changes in the distance between the first electrode and the second electrode and between the first electrode and the third electrode and between the second electrode and the third electrode.

2. The system of claim 1, wherein the electronic control unit is configured to transmit the data via the network to the first circuit and the second circuit to measure capacitance between the first electrode and the second electrode and detect changes in the distance between the first electrode and the second electrode.

3. The system of claim 1, wherein the electronic control unit is configured to transmit the data, which includes at least one of a signal start time, a signal frequency and a spread spectrum set-up, of the signal.

4. The system of claim 1, wherein the network includes a bus connected to at least one of the first circuit and the second circuit and the third circuit.

5. The system of claim 1, wherein the network includes a wireless communications link for communicating to at least one of the first circuit and the second circuit and the third circuit.

6. The system of claim 1, wherein the network includes an inductive coupling configured to communicate to at least one of the first circuit and the second circuit and the third circuit.

7. The system of claim 1, comprising:
an inductive coupling configured to supply power to at least one of the first circuit and the second circuit and the third circuit.

8. The system of claim 1, comprising at least one of:
a power supply connected to the first circuit and at least one of the second circuit and the third circuit; and
a first power supply connected to the first circuit and a second power supply connected to at least one of the second circuit and the third circuit.

9. The system of claim 1, wherein at least one of the first circuit and the third circuit is a transceiver.

10. A method of sensing comprising:
receiving data via a network at a first circuit;
transmitting a first signal from a first electrode directly coupled to the first circuit and based on the data;
receiving the data via the network at a second circuit;
receiving a first current at the second circuit from a second electrode directly coupled to the second circuit and situated a first distance from the first electrode, wherein the first current corresponds to the first signal and the second electrode and the second circuit receive the current based on the data;
transmitting a second signal from the second electrode based on the data;
receiving the data via the network at a third circuit;
receiving a second current at the third circuit from a third electrode directly coupled to the third circuit and situated a second distance from the first electrode and a third distance from the second electrode, wherein the second current corresponds to the first signal and the third electrode and the third circuit receive the second current based on the data;

receiving a third current at the third circuit from the third electrode, wherein the third current corresponds to the second signal and the third electrode and the third circuit receive the third current based on the data;

measuring capacitance between the first electrode and the second electrode based on the first signal and the first current;

measuring capacitance between the first electrode and the third electrode based on the first signal and the second current;

measuring capacitance between the second electrode and the third electrode based on the second signal and the third current;

detecting changes in the distance between the first electrode and the second electrode based on the first signal and the first current;

detecting changes in the distance between the first electrode and the third electrode based on the first signal and the second current; and detecting changes in the distance between the second electrode and the third electrode based on the second signal and the third current.

11. The method of claim 10, comprising:
transmitting the data, which includes at least one of a signal start time, a signal frequency and a spread spectrum set-up, of the signal.

12. The method of claim 10, comprising:
providing power to at least one of the first circuit and the second circuit and the third circuit via inductive coupling.

13. The method of claim 10 comprising:
transmitting the data via at least one of a bus, a wireless communications link and inductive coupling.

14. The system of claim 1, comprising:
a fourth electrode situated a fourth distance from the first electrode and capacitively coupled to the first electrode and situated a fifth distance from the second electrode and capacitively coupled to the second electrode and situated a sixth distance from the third electrode and capacitively coupled to the third electrode; and a fourth circuit configured to receive the data via the network and directly coupled to the fourth electrode to receive a fourth current from the fourth electrode and a fifth current from the fourth electrode and to transmit a third signal via the fourth electrode, wherein the fourth current corresponds to the first signal and the fifth current corresponds to the second signal and the fourth circuit is configured to receive and transmit based on the data, and the third circuit is directly coupled to the third electrode to receive a sixth current from the third electrode that corresponds to the third signal and the electronic control unit is configured to communicate with the fourth circuit via the network and detect changes in the distance between the first electrode and the fourth electrode and between the second electrode and the fourth electrode and between the third electrode and the fourth electrode.

* * * * *